(12) United States Patent
Callant et al.

(10) Patent No.: US 6,603,043 B2
(45) Date of Patent: Aug. 5, 2003

(54) PROCESS FOR THE PREPARATION OF (SCHIFF BASES OF) α-ALKYL-α-AMINO ACID AMIDES

(75) Inventors: Dominique Monique Charles Callant, Houthalen (BE); Daniel Mink, Eupen (BE); Anna Maria Cornelia Francisca Castelijns, Spaubeek (NL)

(73) Assignee: DSM N.V., Te Heerlen (NL)

( * ) Notice: Subject to any disclaimer, the term of this patent is extended or adjusted under 35 U.S.C. 154(b) by 0 days.

(21) Appl. No.: 09/905,637

(22) Filed: Jul. 13, 2001

(65) Prior Publication Data

US 2002/0072634 A1 Jun. 13, 2002

(30) Foreign Application Priority Data

Jul. 14, 2000 (NL) .............................................. 1015715

(51) Int. Cl.$^7$ ............................................. C07C 231/00
(52) U.S. Cl. ....................... 564/139; 564/162; 564/164; 564/165; 564/192; 564/198; 562/443
(58) Field of Search ................. 564/139, 162, 564/164, 165, 192, 198; 562/443

(56) References Cited

U.S. PATENT DOCUMENTS 4,243,814 A * 1/1981 Pascal et al.
4,847,412 A * 7/1989 Boesten et al.
5,047,585 A * 9/1991 Boesten et al.
5,072,041 A * 12/1991 Kamphuis et al.
5,101,036 A * 3/1992 Kamphuis et al.

FOREIGN PATENT DOCUMENTS

GB         1548032    * 4/1979

* cited by examiner

Primary Examiner—Alan L. Rotman
Assistant Examiner—Hector M Reyes
(74) Attorney, Agent, or Firm—Morrison & Foerster LLP

(57) ABSTRACT

Process for the preparation of a Schiff base of an α-alkyl-α-amino acid amide and an aldehyde, wherein the corresponding α-aminonitrile is contacted with a base and the aldehyde and wherein it is ensured that the reagents are in good contact. The Schiff base obtained may be further hydrolysed to form the α-alkyl-α-amino acid amide and the aldehyde.

Preferably a substituted or unsubstituted benzaldehyde is used as the aldehyde. The reaction is preferably carried out in a practically homogeneously mixed phase obtained by using a solvent, for example methanol or ethanol. Preferably NaOH or KOH is used as the base.

18 Claims, No Drawings

PROCESS FOR THE PREPARATION OF (SCHIFF BASES OF) α-ALKYL-α-AMINO ACID AMIDES

The invention relates to a process for the preparation of a Schiff base of an α-alkyl-α-amino acid amide and an aldehyde, wherein the corresponding α-amino nitrile is contacted with a base and the aldehyde and wherein it is ensured that the reagents are in good contact, and to the preparation of the corresponding α-alkyl-α-amino acid amide through hydrolysis of the Schiff base thus obtained.

Surprisingly it has been found that, with the process according to the invention, it is possible to prepare, with a high yield and high selectivity, α-alkyl-α-amino acid amides (which within the framework of this invention represent α-amino acids that do not possess an α-H atom) and the Schiff bases thereof with aldehydes, even when the reaction mixture contains water. This is so surprising because α-amino nitriles are known to undergo retro-Strecker reactions in the presence of water, resulting in the release of cyanide, and that aldehydes, for example benzaldehyde, unlike ketones, very quickly react with the released cyanide and ammonia to form the corresponding α-aminonitrile, phenylglycine nitrile in the case of the benzaldehyde. Hence it was to be expected that use of aldehydes would give rise to the formation of relatively large amounts of α-amino acid amide corresponding to the aldehyde, as an undesired by-product, phenylglycine amide in the case of the benzaldehyde.

A similar process, wherein the conversion of α-H-α-amino nitriles is effected with a ketone and a base, is known from GB-B-1548032. It has however been found that, in the conversion of α-alkyl-α-amino nitriles, this reaction results in no, or only poor conversion. A process corresponding to the process according to the invention appeared also to be suitable for the preparation of α-H-α-amino acid amides from the corresponding α-H-α-amino nitriles.

In the process according to the invention it is ensured that the reagents are contacted with one another as intensively as possible. This can for example be realised by stirring the reaction mixture so that the reaction components are well mixed and no hence demixing takes place, whether or not in the presence of a phase-transfer catalyst. Preferably the reaction is carried out in the presence of a solvent, it being ensured that the reaction takes place entirely, or to a substantial extent, in a homogeneous phase. As commonly known, this can for example be realised by the choice of the type of solvent and its relative amount with respect to the reagents. Suitable solvents are for example alcohols, glycols, ethers or other polar organic solvents, for example dimethylformamide (DMF), acetonitrile or hexamethylphosphortriamide (HMPTA). Preferably use is made of methanol or ethanol.

The type of aldehyde to be used is preferably chosen such that no or only minor undesired side reactions, for example aldol condensation, take place. Preferably, use is made of an aromatic aldehyde, in particular a substituted or unsubstituted benzaldehyde, or a sterically hindered aldehyde, for example pivaldehyde. Suitable substituents for the benzaldehyde are for example alkyl or alkoxy groups (1–5 C atoms), halogens (F, Cl, Br) or a nitro group.

Examples of α-amino acid amides that may particularly suitably be prepared with the process according to the invention are α-alkyl-α-amino acid amides, with the alkyl representing for example an alkyl group with 1–6 C atoms which may be substituted, for instance with an alkoxy group, preferably methyl or ethyl, in particular α-alkyl-α-(hetero) aryl glycine amides and α,α'-dialkylglycine amides, in which (hetero)aryl represents a substituted or unsubstituted phenyl, or heteroaromatic ring, for instance a pyridine ring, more in particular α-methyl-α-phenylglycine amide and α-ethyl-α-butylglycine amide. Suitable substituents for the (hetero)aryl group are for instance an alkyl group (1–6 C atoms), an alkoxy group (1–6 C atoms), halogen or hydroxy.

The reaction conditions under which the process according to the invention is carried out are not very critical. The reaction conditions are preferably chosen so that there is as little possible risk of a retro-Strecker reaction taking place.

The type of base to be used is not very critical. Bases that are suitable for use are for example alkali metal, alkaline earth metal, ammonium or quaternary ammonium hydroxides or carbonates. Preferably use is made of NaOH or KOH, for example as a solution in water.

The temperature at which the Schiff base is prepared is not very critical and lies between for example −10 and 100° C., preferably between 0 and 70° C., in particular between 10 and 40° C. The pressure at which the reaction is carried out is not critical; for practical reasons the reaction will usually be carried out at atmospheric pressure.

The amount of aldehyde to be used is preferably chosen to be more than 1 equivalent relative to the amount of aminonitrile, preferably between 1 and 2 equivalents. Larger amounts can in principle be used, but will not normally prove advantageous in practice.

The amount of base to be used may vary within a wide range and will preferably lie between 0.05 and 1 equivalent, in particular between 0.2 and 0.5 equivalent relative to the amount of aminonitrile.

The order in which the reagents are dosed may in principle be chosen freely. Depending on the stability of the aminonitrile, it may prove advantageous to dose the aminonitrile to the other reagents. This will ensure that the concentration of the aminonitrile in the reaction mixture remains as low as possible, and hence the risk of a retro-Strecker reaction will remain as low as possible.

Optionally, the Schiff base of the α-alkyl-α-amino acid amide and the aldehyde thus obtained may subsequently be hydrolysed. This can for example be realised by causing the Schiff base to react with water in the presence of an acid, for example a mineral acid, in particular sulphuric acid or hydrochloric acid. The hydrolysis may in principle also be carried out under basic conditions, but this is not preferred.

The invention will be further elucidated with reference to examples, without being limited thereby.

EXAMPLE I 326 grams of methanol and 426 grams of benzaldehyde were introduced into a double-walled glass reactor fitted with a mechanical stirring device, a dosing funnel, a bottom drain and a thermostat. To this were then with stirring, added, 172 grams of a 25 wt. % aqueous solution of NaOH, which caused the temperature to rise from 22° C. to 30° C. Immediately hereafter the dosage, with stirring, of 400 grams of crude aminonitrile was started. The crude amino nitrile (79.4 wt. % α-amino-α-methylphenylacetonitrile and 19.2 wt. % acetophenone) was obtained in a Strecker reaction of acetophenone with ammonia and hydrocyanic acid. The total dosage time was 45 minutes. During the dosage the temperature of the reaction mixture was kept at 35–38° C. (by means of cooling).

After all the aminonitrile had been dosed, 675 grams of toluene was added to the reaction mixture, after which the reaction mixture was heated to 55° C. (with stirring). The stirring was then stopped, after which (at 55° C.) phase separation took place. The aqueous bottom layer was separated. 598 grams of a 10 wt. % NaOH solution was added to the organic phase, after which the reaction mixture was heated to 55° C. with stirring. The stirring was then stopped, after which phase separation took place. The aqueous bottom layer was separated.

Next, 846 grams of water followed by concentrated sulphuric acid were added (with stirring) at 55° C. to the organic phase, which contained the Schiff base of α-amino-α-methylphenylacetamide and benzaldehyde, until the reaction mixture had a pH of 2.1 (required: 116 grams of sulphuric acid). Then the phases were separated. The aqueous bottom layer (1310 grams) was analysed with the aid of HPLC and contained 29 wt. % α-amino-αmethylphenylacetamide.½H$_2$SO$_4$. In addition, only very small amounts (0.1 wt. %) of the sulphuric acid salts of phenylglycinamide and phenylglycine were found. The degree of conversion of α-amino-α-methylphenylacetonitrile into α-amino-αmethylphenylacetamide was approx. 82%.

Comparative Experiment 1

326 grams of methanol and 220 grams of acetone were introduced into a double-walled glass reactor fitted with a mechanical stirring device, a dosing funnel, a bottom drain and a thermostat. To this was then added, with stirring, 172 grams of a 25% aqueous solution of NaOH, which caused the temperature to rise from 22° C. to 30° C. Immediately hereafter the dosage, with stirring, of 400 grams of (crude) aminonitrile (79.4 wt. % α-amino-α-methylphenylacetonitrile and 19.2 wt. % acetophenone) was started. The dosage time was 50 minutes. During the dosage the temperature of the reaction mixture increased from 30° C. to 40° C. This was followed by an after-reaction for 30 minutes, during which the temperature of the reaction mixture was increased to 55° C.

Next, 672 grams of toluene was dosed to the reaction mixture and the reaction mixture was stirred for 15 minutes at 55° C. The stirring was then stopped, after which phase separation took place. The aqueous bottom layer was separated. Then 598 grams of a 10 wt. % NaOH solution was dosed to the organic phase, after which the reaction mixture was heated to 55° C. with stirring. The stirring was then stopped and phase separation took place. The aqueous bottom layer was separated. Then 850 grams of water followed by concentrated sulphuric acid were added, with stirring, at 55° C. until the reaction mixture had a pH of 2.06 (required: 54 grams of sulphuric acid). Then the phases were separated. The aqueous bottom layer (1007 grams) was analysed with the aid of HPLC and contained 0.3 wt. % α-amino-α-methylphenylacetamide.½H$_2$SO$_4$. The degree of conversion of α-amino-α-methylphenylacetonitrile into α-amino-α-methylphenylacetamide was approx. 0.7%.

Comparative Experiment 2

672 grams of toluene and 426 grams of benzaldehyde were introduced into a double-walled glass reactor fitted with a mechanical stirring device, a dropping funnel, a bottom drain and a thermostat. Next, 172 grams of a 25% aqueous solution of NaOH was added, with stirring, which caused the temperature to rise to 30° C. Immediately hereafter, 400 grams of (crude) aminonitrile (79.4 wt. % α-amino-α-methylphenylacetonitrile and 19.2 wt. % acetophenone) was dosed to the reaction mixture, with stirring. The dosage time was 45 minutes. During the dosage the temperature of the reaction mixture increased from 30° C. to 40° C. Next, an after-reaction took place for 30 minutes, in which the temperature of the reaction mixture was increased to 55° C.

Then the stirring was stopped, after which phase separation took place. The aqueous bottom layer was separated. Next, 598 grams of a 10 wt. % NaOH solution was dosed to the organic phase, after which the reaction mixture was heated to 55° C. with stirring. Then the stirring was stopped and phase separation took place. The aqueous bottom layer was separated. Next, 700 grams of water followed by concentrated sulphuric acid were dosed (with stirring) at 55° C. until the reaction mixture had a pH of 2.01 (required: 72 grams of sulphuric acid). Then the phases were separated. The aqueous bottom layer (839 grams) was analysed with the aid of HPLC and was found to contain 6.5 wt. % α-amino-α-methylphenylacetamide.½H$_2$SO$_4$. This water layer also contained 0.16 wt. % of the sulphuric acid salt of phenylglycine amide. The degree of conversion of α-amino-α-methylphenylacetonitrile into α-amino-α-methylphenylacetamide was approx. 11.8%.

EXAMPLE II 20.2 grams of methanol, 6.7 grams of benzaldehyde and 3.4 grams of a 25 wt. % aqueous NaOH solution were successively introduced into a 100-ml round-bottomed flask fitted with a mechanical stirring device and a dosing funnel. This was immediately followed by the dosage, with stirring, at room temperature, of 10.1 grams of crude aminonitrile (74.3 wt. % 3-amino-3-cyanoheptane and 19.4 wt. % 3-heptanone) obtained in a Strecker reaction between 3-heptanone and ammonia and hydrocyanic acid. The dosage time was 3.5 hours. The reaction mixture formed a homogeneous phase. The reaction mixture was subsequently stirred for another 13.5 hours at room temperature. The reaction mixture was then analysed with the aid of HPLC and was found to contain 28.8 wt. % of the Schiff base of benzaldehyde and 2-amino-2-ethyihexanoic acid amide. The yield was 88%.

What is claimed is:

1. A process for the preparation of a Schiff base formed with an α-alkyl-α-amino acid amide (which is an α amino acid amide which lacks any H coupled directly to the α carbon), and an aldehyde, comprising reacting the corresponding α-alkyl-α-aminonitrile with a base and the aldehyde with sufficient mixing that the reaction mixture is maintained without de-mixing in a substantially homogeneous condition.

2. A process to prepare an α-alkyl-α-amino acid amide wherein the process of claim 1 further comprises hydrolyzing the Schiff base obtained to form the α-alkyl-α-amino acid amide and the aldehyde.

3. The process of claim 1, wherein the alkyl is selected from the group consisting of methyl and ethyl.

4. The process of claim 3, wherein the α-alkyl-α-amino acid amide is α-methyl-α-phenylglycineamide.

5. The process of claim 3, wherein the α-alkyl-α-amino acid amide is 2-amino-2-ethylhexanoic acid amide.

6. The process of claim 1, wherein the aldehyde is selected from the group consisting of a substituted benzaldehyde and an unsubstituted benzaldehyde.

7. The process of claim 1, wherein said homogeneous condition is further maintained by using a solvent.

8. The process of claim 7, wherein the solvent is selected from the group consisting of methanol and ethanol.

9. The process of claim 1, wherein the base is selected from the group consisting of NaOH and KOH.

10. A process for the preparation of a Schiff base formed with an α-alkyl-α-amino acid amide which is an α amino acid amide which lacks any H coupled directly to the α carbon, and an aromatic aldehyde, comprising reacting the corresponding α-alkyl-αaminonitrile with a base and the aromatic aldehyde with sufficient mixing that the reaction mixture is maintained without de-mixing in a substantially homogeneous condition.

11. A process to prepare an α-alkyl-α-amino acid amide wherein the process of claim 10 further comprises hydrolyzing the Schiff base obtained to form the α-alkyl-α-amino acid amide and the aromatic aldehyde.

12. The process in claim 10, wherein the alkyl is selected from the group consisting of methyl and ethyl.

13. The process of claim 12, wherein the α-alkyl-α-amino acid amide is α-methyl-α-phenylglycineamide.

14. The process of claim 12, wherein the α-alkyl-α-amino acid amide is 2-amino-2-ethylhexanoic acid amide.

15. The process of claim 10, wherein the aromatic aldehyde is selected from the group consisting of a substituted benzaldehyde and an unsubstituted benzaldehyde.

16. The process of claim 10, wherein said homogenous condition is further maintained by using a solvent.

17. The process of claim 16, wherein the solvent is selected from the group consisting of methanol and ethanol.

18. The process of claim 10, wherein the base is selected from the group consisting of NaOH and KOH.

* * * * *